(12) United States Patent
Stegmann et al.

(10) Patent No.: US 8,562,862 B2
(45) Date of Patent: *Oct. 22, 2013

(54) WATER ABSORBING MATERIAL

(75) Inventors: Veit Stegmann, Mannheim (DE); Klemens Massonne, Bad Dürkheim (DE); Franz Niklaus Windlin, Heidelberg (DE); Reinhold Schwalm, Wachenhaim (DE); Dieter Hermeling, Böhl-Iggelheim (DE); Thomas Daniel, Waldsee (DE); Stefan Bruhns, Mannheim (DE)

(73) Assignee: BASF SE, Ludwigshafen (DE)

( * ) Notice: Subject to any disclaimer, the term of this patent is extended or adjusted under 35 U.S.C. 154(b) by 150 days.

This patent is subject to a terminal disclaimer.

(21) Appl. No.: 13/060,347

(22) PCT Filed: Sep. 8, 2009

(86) PCT No.: PCT/EP2009/061633
§ 371 (c)(1),
(2), (4) Date: Feb. 23, 2011

(87) PCT Pub. No.: WO2010/029074
PCT Pub. Date: Mar. 18, 2010

(65) Prior Publication Data
US 2011/0178251 A1  Jul. 21, 2011

(30) Foreign Application Priority Data
Sep. 12, 2008 (EP) .................................... 08164216

(51) Int. Cl.
*B01J 20/04* (2006.01)
*B01J 20/16* (2006.01)
*B01J 20/18* (2006.01)
*C09K 3/00* (2006.01)
*C08J 3/28* (2006.01)
*A61L 15/60* (2006.01)

(52) U.S. Cl.
USPC ........... 252/194; 524/403; 524/407; 524/413; 524/431; 524/558; 427/508

(58) Field of Classification Search
USPC .......... 252/194; 524/403, 407, 413, 431, 558; 427/508
See application file for complete search history.

(56) References Cited

U.S. PATENT DOCUMENTS

| | | | |
|---|---|---|---|
| 4,734,478 A | 3/1988 | Tsubakimoto et al. | |
| 4,783,510 A | 11/1988 | Saotome | |
| 6,831,122 B2 * | 12/2004 | Daniel et al. | 524/417 |
| 7,166,356 B2 | 1/2007 | Flohr | |
| 7,285,615 B2 * | 10/2007 | Adachi et al. | 526/319 |
| 7,449,219 B2 | 11/2008 | Flohr | |
| 7,576,138 B2 | 8/2009 | Flohr et al. | |
| 7,838,569 B2 | 11/2010 | Flohr et al. | |
| 7,879,923 B2 | 2/2011 | Matsumoto et al. | |
| 2004/0048955 A1 * | 3/2004 | Wada et al. | 524/9 |
| 2004/0077796 A1 * | 4/2004 | Daniel et al. | 525/360 |
| 2004/0176544 A1 | 9/2004 | Mertens et al. | |
| 2005/0209352 A1 * | 9/2005 | Dairoku et al. | 521/50 |
| 2007/0149691 A1 * | 6/2007 | Ishizaki et al. | 524/500 |
| 2007/0238806 A1 | 10/2007 | Mitsukami et al. | |
| 2007/0254177 A1 | 11/2007 | Smith et al. | |
| 2008/0032888 A1 | 2/2008 | Nakamura et al. | |
| 2008/0033385 A1 | 2/2008 | Grota | |
| 2008/0269372 A1 * | 10/2008 | Dairoku et al. | 523/149 |
| 2009/0270538 A1 * | 10/2009 | Ikeuchi et al. | 524/115 |
| 2009/0298963 A1 | 12/2009 | Matsumoto et al. | |
| 2011/0046279 A9 * | 2/2011 | Ikeuchi et al. | 524/115 |
| 2011/0275513 A1 * | 11/2011 | Tian et al. | 502/402 |

FOREIGN PATENT DOCUMENTS

| | | |
|---|---|---|
| EP | 0248437 A2 | 12/1987 |
| EP | 1504772 A1 | 2/2005 |
| EP | 1757648 A1 | 2/2007 |
| JP | 2007-321008 A | 12/2007 |
| WO | WO-2005/108472 A1 | 11/2005 |
| WO | WO-2006/062253 A1 | 6/2006 |
| WO | WO-2006/062258 A2 | 6/2006 |
| WO | WO-2007/024926 A1 | 3/2007 |
| WO | WO-2008/018009 A1 | 2/2008 |

OTHER PUBLICATIONS

International Search Report from corresponding International Application No. PCT/EP2009/061633, mailing date Mar. 10, 2010.

* cited by examiner

*Primary Examiner* — Joseph D Anthony
(74) *Attorney, Agent, or Firm* — Marshall, Gerstein & Borun LLP

(57) ABSTRACT

The present invention relates to a water-absorbing material obtainable by a process comprising the steps of A) treating a particulate, non-surface-crosslinked, water-absorbing polymer with a mixture comprising an aqueous solvent and at least one salt of a transition metal and B) irradiating the polymer treated according to A) with UV radiation, to a process for its production and to articles comprising the water-absorbing material.

11 Claims, No Drawings

WATER ABSORBING MATERIAL

CROSS-REFERENCE TO RELATED APPLICATIONS

This is the U.S. national phase of International Application No. PCT/EP2009/061633, filed Sep. 8, 2009, which claims the benefit of European Patent Application No. 08164216.7, filed Sep. 12, 2008.

NAMES OF PARTIES TO A JOINT RESEARCH AGREEMENT

This application arises under an agreement between BASF SE and The Procter & Gamble Company made on Sep. 9, 2008.

The present invention relates to a water-absorbing material, to a process for its production and to its use.

Water-absorbing polymers are known. For such materials, names such as "highly swellable polymer" "hydrogel" (often also used for the dry form), "hydrogel-forming polymer", "superabsorbent polymer", "superabsorbent", "absorbent gel-forming material", "swellable resin", "water-absorbing resin" or the like are also common. These polymers are crosslinked hydrophilic polymers, especially polymers formed from (co)polymerized hydrophilic monomers, graft (co)polymers of one or more hydrophilic monomers on a suitable graft base, crosslinked cellulose ethers or starch ethers, crosslinked carboxymethylcellulose, partly crosslinked polyalkylene oxide or natural products swellable in aqueous liquids, for example guar derivatives, water-absorbing polymers based on partly neutralized acrylic acid being the most widespread. The essential properties of water-absorbing polymers are their ability to absorb several times their own weight of aqueous liquids and not to release the liquid again, even under a certain pressure. The water-absorbing polymer, which is used in the form of a dry powder, is converted to a gel when it absorbs liquid and correspondingly to a hydrogel when it absorbs water, as is customary. By far the most important field of use of water-absorbing polymers is the absorption of body fluids. Water-absorbing polymers are used, for example, in diapers for infants, incontinence products for adults or feminine hygiene products. Other fields of use are, for example, those as water-retaining agents in market gardening, as a water store for protection from fire, for liquid absorption in food packaging or quite generally for absorption of moisture.

It is known that water-absorbing polymers can be crosslinked on their surface with reactive compounds. This can be done by treatment with organic compounds such as polyols. At high temperature and with a high residence time, these react with the free carboxylate groups on the surface of the polymer, such as by esterification for the example of the polyols. Such surface-crosslinkings are described, for example, in U.S. Pat. No. 4,734,478.

A further route is the treatment with polyvalent metal cations such as aluminum salts. In this case, the free carboxylate groups on the surface of the polymer form salts with the polyvalent cations. Such surface crosslinkings are described, for example in WO-A-2005/108472.

Additionally known are processes for crosslinking the surface, in which free-radical polymerization initiators, if appropriate together with unsaturated organic compounds and additives, are applied and treated with high-energy radiation or thermal energy. Such surface crosslinkings are described, for example, in WO-A-2006/062253, WO-A-2006/062258, EP 1504772, EP 1757648, JP 2007-321008 and US 2007/0238806 or EP 0248437.

In addition, WO 2007/024926 describes a process for producing surface-crosslinked superabsorbents, in which a non-surface-crosslinked water-absorbing dried polymer powder, if appropriate with addition of an aqueous solution of a photoinitiator, is treated with VUV radiation in a drum.

WO 2008/018009 teaches the treatment of an already surface-crosslinked water-absorbing dried polymer powder with semiconductor materials such as $TiO_2$ and subsequent irradiation of the particles, in order to increase the hydrophilicity of the surface.

However, it has been found that these treatments lead to surface-modified polymers but not with the desired absorption properties. Furthermore, a process is to be provided with a good space-time yield.

It is therefore an object of the invention to provide a process for producing water-absorbing polymer particles with high absorption under pressure (AUP) within a short processing time and without thermal stress.

Accordingly, a water-absorbing material has been found, obtainable by a process comprising the steps of A) treating a particulate, non-surface-crosslinked, water-absorbing polymer with a mixture comprising an aqueous solvent and at least one salt of a transition metal and B) irradiating the polymer treated according to A) with UV radiation, as have a process for its production and articles comprising the water-absorbing material.

Processes for producing non-surface-crosslinked water-absorbing polymers, also referred to hereinafter as base polymer, are known.

Water-absorbing polymers are obtained, for example, by polymerizing a monomer solution comprising a) at least one ethylenically unsaturated monomer bearing acid groups, b) at least one crosslinker, c) if appropriate one or more ethylenically and/or allylically unsaturated monomers copolymerizable with the monomer a) and d) if appropriate one or more water-soluble polymers, on to which the monomers a), b) and, if appropriate, c) can be grafted at least partly.

Suitable monomers a) are, for example, ethylenically unsaturated carboxylic acids, such as acrylic acid, methacrylic acid, maleic acid, fumaric acid and itaconic acid, or derivatives thereof, such as acrylamide, methacrylamide, acrylic esters and methacrylic esters. Particularly preferred monomers are acrylic acid and methacrylic acid. Very particular preference is given to acrylic acid.

The monomers a), especially acrylic acid, comprise preferably up to 0.025% by weight of a hydroquinone monoether. Preferred hydroquinone monoethers are hydroquinone monomethyl ether (MEHQ) and/or tocopherols.

Tocopherol is understood to mean compounds of the following formula

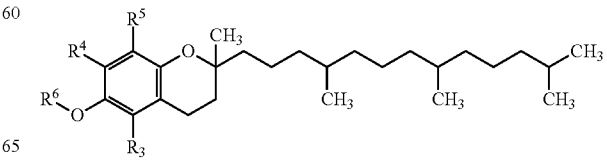

where $R^3$ is hydrogen or methyl, $R^4$ is hydrogen or methyl, $R^5$ is hydrogen or methyl and $R^6$ is hydrogen or an acyl radical having from 1 to 20 carbon atoms.

Preferred radicals for $R^6$ are acetyl, ascorbyl, succinyl, nicotinyl and other physiologically compatible carboxylic acids. The carboxylic acids may be mono-, di- or tricarboxylic acids.

Preference is given to alpha-tocopherol where $R^3=R^4=R^5=$methyl, especially racemic alpha-tocopherol. $R^6$ is more preferably hydrogen or acetyl. Especially preferred is RRR-alpha-tocopherol.

The monomer solution comprises preferably at most 130 ppm by weight, more preferably at most 70 ppm by weight, preferably at least 10 ppm by weight, more preferably at least 30 ppm by weight, especially around 50 ppm by weight, of hydroquinone monoether, based in each case on acrylic acid, acrylic acid salts also being counted as acrylic acid. For example, the monomer solution can be prepared by using an acrylic acid having an appropriate content of hydroquinone monoether.

The crosslinkers b) are compounds having at least two polymerizable groups which can be polymerized by free-radical means into the polymer network. Suitable crosslinkers b) are, for example ethylene glycol dimethacrylate, diethylene glycol diacrylate, allyl methacrylate, trimethylolpropane triacrylate, triallylamine tetraallyloxyethane, as described in EP 530 438 A1, di- and triacrylates, as described in EP 547 847 A1, EP 559 476 A1, EP 632 068 A1, WO 93/21 237 A1, WO 03/104 299 A1, WO 03/104 300 A1, WO 03/104 301 A1 and DE 103 31 450 A1, mixed acrylates, which, as well as acrylate groups, comprise further ethylenically unsaturated groups, as described in DE 103 31 456 A1 and WO 04/013 064 A2, or crosslinker mixtures, as described, for example, in DE 195 43 368 A1, DE 196 46 484 A1, WO 90/15 830 A1 and WO 02/032 962 A2.

Suitable crosslinkers b) are especially N,N'-methylenebisacrylamide and N,N'-methylenebismethacrylamide, esters of unsaturated mono- or polycarboxylic acids of polyols, such as diacrylate or triacrylate, for example butanediol diacrylate, butanediol dimethacrylate, ethylene glycol diacrylate or ethylene glycol dimethacrylate, and also trimethylolpropane triacrylate and allyl compounds, such as allyl(meth)acrylate, triallyl cyanurate, diallyl maleate, polyallyl esters, tetraallyloxyethane, triallylamine, tetraallylethylenediamine, allyl esters of phosphoric acid, and vinylphosphonic acid derivatives, as described, for example, in EP 343 427 A2. Further suitable crosslinkers b) are pentaerythritol diallyl ether, pentaerythritol triallyl ether and pentaerythritol tetraallyl ether, polyethylene glycol diallyl ether, ethylene glycol diallyl ether, glyceryl diallyl ether and glyceryl triallyl ether, polyallyl ethers based on sorbitol, and ethoxylated variants thereof. In the process according to the invention, it is possible to use di(meth)acrylates of polyethylene glycols, where the polyethylene glycol used has a molecular weight between 300 and 1000.

Particularly advantageous crosslinkers b) are, however, di- and triacrylates of 3- to 15-tuply ethoxylated glycerol, of 3- to 15-tuply ethoxylated trimethylolpropane, of 3- to 15-tuply ethoxylated trimethylolethane, especially di- and triacrylates of 2- to 6-tuply ethoxylated glycerol or trimethylolpropane, of 3-tuply propoxylated glycerol or trimethylolpropane, and of 3-tuply mixed ethoxylated or propoxylated glycerol or trimethylolpropane, of 15-tuply ethoxylated glycerol or trimethylolpropane, and of 40-tuply ethoxylated glycerol, trimethylol ethane or trimethylol propane.

Very particularly preferred crosslinkers b) are the polyethoxylated and/or propoxylated glycerols which have been esterified with acrylic acid or methacrylic acid to give di- or triacrylates, as described, for example, in WO 03/104 301 A1. Particularly advantageous are di- and/or triacrylates of 3- to 10-tuply ethoxylated glycerol. Very particularly preferred are di- or triacrylates of 1- to 5-tuply ethoxylated and/or propoxylated glycerol. Most preferred are the triacrylates of 3- to 5-tuply ethoxylated and/or propoxylated glycerol. These feature particularly low residual contents (typically below 10 ppm by weight) in the water-absorbing polymers, and the aqueous extracts of the water-absorbing polymers prepared with them have an almost unchanged surface tension (typically at least 0.068 N/m) compared to water at the same temperature.

Ethylenically unsaturated monomers c) copolymerizable with the monomers a), are, for example, acrylamide, methacrylamide, crotonamide, dimethylaminoethyl methacrylate, dimethylaminoethyl acrylate, dimethylaminopropyl acrylate, diethylaminopropyl acrylate, dimethylaminobutyl acrylate, dimethylaminoethyl methacrylate, diethylaminoethyl methacrylate, dimethylaminoneopentyl acrylate and dimethylaminoneopentyl methacrylate.

The water-soluble polymers d) used may be polyvinyl alcohol, polyvinylpyrrolidone, starch, starch derivatives, polyglycols, polymers which have been formed in a formal sense completely or partly from vinylamine monomers, such as partly or fully hydrolyzed polyvinylamide (so-called "polyvinylamine") or polyacrylic acids, preferably poly-vinyl alcohol and starch.

The polymerization is, if appropriate, performed in the presence of customary polymerization regulators. Suitable polymerization regulators are, for example, thio compounds, such as thioglycolic acid, mercapto alcohols, e.g. 2-mercaptoethanol, mercaptopropanol and mercaptobutanol, dodecyl mercaptan, formic acid, ammonia and amines, e.g. ethanolamine, diethanolamine, triethanolamine, triethylamine, morpholine and piperidine.

The monomers (a), (b) and, if appropriate (c) are, if appropriate, in the presence of the water-soluble polymers d), (co)polymerized with one another in from 20 to 80% by weight, preferably from 20 to 50% by weight, especially 30 to 45% by weight, aqueous solution in the presence of polymerization initiators. The polymerization initiators used may be all compounds which decompose to free radicals under the polymerization conditions, for example peroxides, hydroperoxides, hydrogen peroxide, persulfates, azo compounds and the so-called redox initiators. Preference is given to the use of water-soluble initiators. In some cases, it is advantageous to use mixtures of different polymerization initiators, for example, mixtures of hydrogen peroxide and sodium peroxodisulfate or potassium peroxodisulfate. Mixtures of hydrogen peroxide and sodium peroxodisulfate can be used in any desired ratio. Suitable organic peroxides are, for example, acetylacetone peroxide, methyl ethyl ketone peroxide, tert-butyl hydroperoxide, cumene hydroperoxide, tert-amyl perpivalate, tert-butyl perpivalate, tert-butyl perneohexanoate, tert-butyl perisobutyrate, tert-butyl per-2-ethylhexanoate, tert-butyl perisononanoate, tert-butyl permaleate, tert-butyl perbenzoate, tert-butyl per-3,5,5-trimethylhexanoate and tert-amyl perneodecanoate. Further suitable polymerization initiators are azo initiators, for example 2,2'-azobis-(2-amidinopropane)dihydrochloride, 2,2'-azobis-(N,N-dimethylene)isobutyramidine dihydrochloride, 2-(carbamoylazo)isobutyronitrile and 4,4'-azobis(4-cyanovaleric acid). The polymerization initiators mentioned are used in customary amounts, for example in amounts of from 0.01 to 5 mol %, preferably from 0.1 to 2 mol %, based on the monomers to be polymerized.

The redox initiators comprise, as the oxidizing component at least one of the above-specified per compounds and a reducing component, for example ascorbic acid, glucose, sorbose, ammonium hydrogensulfite, sulfite, thiosulfate, hyposulfite, pyrosulfite or sulfide, or alkali metal hydrogen sulfite, sulfite, thiosulfate, hyposulfite, pyrosulfite or sulfide, metal salts such as iron(II) ions or silver ions, or sodium hydroxymethylsulfoxylate. Preference is given to using, as the reducing component of the redox initiator, ascorbic acid or sodium pyrosulfite. Based on the amount of monomers used in the polymerization, from $1 \cdot 10^{-5}$ to 1 mol % of the reducing component of the redox initiator and from $1 \cdot 10^{-5}$ to 5 mol % of the oxidizing component are used. Instead of the oxidizing component or in addition, it is also possible to use one or more water-soluble azo initiators.

Preference is given to using a redox initiator consisting of hydrogen peroxide, sodium peroxodisulfate and ascorbic acid. For example, these components are used in the concentrations of $1 \cdot 10^{-2}$ mol % of hydrogen peroxide, 0.084 mol % of sodium peroxodisulfate and $2.5 \cdot 10^{-3}$ mol % of ascorbic acid, based on the monomers.

The aqueous monomer solution may comprise the initiator in dissolved or dispersed form. The initiators may, however, also be supplied to the polymerization reactor separately from the monomer solution.

For optimal action, the preferred polymerization inhibitors require dissolved oxygen. Therefore, the polymerization inhibitors can be freed of dissolved oxygen before the polymerization by inertization, i.e. blowing an inert gas through, preferably nitrogen. This is done by means of inert gas which can be introduced in co-current, counter-current or intermediate angles of entry. Good mixing can be achieved, for example with nozzles, static or dynamic mixers or bubble columns. The oxygen content of the monomer solution is preferably lowered before the polymerization to less than 1 ppm by weight, more preferably to less than 0.5 ppm by weight. The monomer solution is, if appropriate, conducted through the reactor with an inert gas stream.

The preparation of a suitable base polymer and further suitable hydrophilic ethylenically unsaturated monomers a) are described, for example in DE 199 41 423 A1, EP 686 650 A1, WO 01/45 758 A1 and WO 03/104 300 A1.

Non-surface-crosslinked water-absorbing polymers (base polymers) are typically obtained by polymerizing an aqueous monomer solution and, if appropriate, a subsequent comminution of the hydrogel. Suitable preparation processes are described in the literature. base polymers are obtained, for example, by:
  gel polymerization in a batch process or tubular reactor and subsequent comminution in a meat grinder, extruder or kneader, as described, for example, in EP 445 619 A2 and DE 198 46 413 A1;
  polymerization in a kneader, continuous comminution being effected by means of, for example counter-rotating kneader shafts, as described in WO 01/38 402 A1;
  polymerization on a belt and subsequent comminution in a meat grinder, extruder or kneader as described in EP 955 086 A2, DE 38 25 366 A1 or U.S. Pat. No. 6,241,928;
  emulsion polymerization, which already affords bead polymers of relatively narrow gel size distribution, as described in EP 457 660 A1;
  droplet polymerization as described in WO2006/079631 A1;
  in-situ polymerization of a fabric layer, which, usually in continuous operation, has been sprayed beforehand with aqueous monomer solution and then subjected to a photo-polymerization, as described in WO 02/94 328 A2, WO 02/94 329 A1).

With regard to details of the process procedure, reference is hereby made explicitly to the documents cited. The reaction is preferably carried out in a kneader or on a belt reactor.

The preparation process for water-absorbing polymers which is preferred for economic reasons and is therefore currently customary is that of continuous gel polymerization. First, a monomer solution is prepared by adding the neutralizing agent, optional co-monomers and/or further assistants to the acrylic acid solution at different times and/or spatially separately, and then transferring the mixture into the reactor, or actually initially charging it in the reactor. As the last addition, the initiator system is metered in at the start of the polymerization. In the continuous polymerization process which follows, the reaction proceeds to give the polymer gel (i.e. the polymer swollen to a gel in the solvent of the polymerization—typically water), which in the case of a kneader polymerization, is already comminuted in advance. The polymer gel is subsequently dried and, if required, also crushed, ground and screened, and transferred to further surface treatment.

The acid groups of the resulting hydrogels are typically partly neutralized, generally to an extent of at least 25 mol %, preferably to an extent of at least 27 mol % and more preferably to an extent of at least 40 mol %, and generally at most 85 mol %, preferably at most 80 mol % and more preferably at most 75 mol %, for which the customary neutralizing agents can be used, preferably alkali metal hydroxides, alkali metal oxides, alkali metal carbonates or alkali metal hydrogencarbonates, and mixtures thereof. Instead of alkali metal salts, it is also possible to use ammonium salts. Sodium and potassium are particularly preferred as alkali metals, but very particular preference is given to sodium hydroxide, sodium carbonate or sodium hydrogencarbonate and mixtures thereof. Typically, the neutralization is achieved by mixing in the neutralizing agent as an aqueous solution or preferably also as a solid. For example, sodium hydroxide with water content significantly below 50% by weight may be present as a waxy material with a melting point above 23° C. In this case, metered addition as piece material or a melt at elevated temperature is possible.

The neutralization can be carried out after the polymerization, at the hydrogel stage. However, it is also possible to carry out the neutralization to the desired degree of neutralization entirely or partly before the polymerization. In the case of partial neutralization before the polymerization, generally at least 10 mol %, preferably at least 15 mol %, and generally at most 40 mol %, preferably at most 30 mol % and more preferably at most 25 mol % of the acid groups in the monomers used are neutralized before the polymerization, by adding a portion of the neutralizing agent actually to the monomer solution. The desired final degree of neutralization in this case is not established until toward the end of or after the polymerization, preferably at the hydrogel stage, before it is dried. The monomer solution is neutralized by mixing in the neutralizing agent. The hydrogel can be mechanically comminuted in the course of neutralization, for example by means of a meat grinder or comparable apparatus for comminuting gellike materials, in which case the neutralizing agent is sprayed on, scattered over or poured on and then mixed in carefully. To this end, the resulting gel material can be subjected to meat grinding several times more for homogenization. Preferably, the monomer solution is adjusted to the desired final degree of neutralization by adding the neutralizing agent before polymerization.

The gels obtained from the polymerization are, if appropriate, kept for a certain time, for example at least 30 minutes, preferably at least 60 minutes and more preferably at least 90 minutes, and generally at most 12 hours, preferably at most 8 hours and more preferably at most 6 hours, at a temperature of generally at least 50° C. and preferably at least 70° C. and generally at most 130° C. and preferably at most 100° C., which often allows their properties to be improved further.

The neutralized hydrogel is then dried with a belt drier or roll drier until the residual moisture content is preferably below 15% by weight, especially below 10% by weight, the water content being determined by the EDANA (European Disposables and Non-wovens Association) recommended test method No. 430.2-02 "Moisture Content". The dry water-absorbing polymer consequently comprises up to 15% by weight of moisture, preferably at most 10% by weight. What is crucial for the classification as "dry" is especially sufficient free flow for handling as a powder (for instance for pneumatic delivery, transferring, screening or other process steps from solid-state process technology). If appropriate, for drying, it is also possible to use a fluidized bed drier or a heated ploughshare mixer. In order to obtain particularly colorless products, it is advantageous in the course of drying of this gel to ensure that the evaporating water is rapidly transported away. To this end, the drier temperature has to be optimized, the air supply and removal have to be controlled, and sufficient venting has to be ensured in each case. By its nature, the higher the solids content of the gel, the simpler the drying and the more colorless the product. The solvent content in the polymerization is therefore adjusted such that the solids content of the gel before the drying is therefore generally at least 20% by weight, preferably at least 25% by weight and more preferably at least 30% by weight, and generally at most 90% by weight, preferably at most 85% by weight and more preferably at most 80% by weight. It is particularly advantageous to vent the drier with nitrogen or another non-oxidizing inert gas. If appropriate though, it is also possible simply to lower only the partial pressure of the oxygen during the drying, in order to prevent oxidative yellowing processes. In general, however, even sufficient venting and removal of the water vapor lead to a product which is still acceptable. With regard to color and product quality, a very short drying time is generally advantageous.

The dried hydrogel (which is no longer a gel—even though it is still referred to as such—but rather a dry polymer with superabsorbent properties) is preferably ground and screened. For the grinding, roll mills, pin mills, hammer mills, cutting mills or vibratory mills are typically used, and, for the screening, gravity screening machines, gyratory screening machines, tumbling screening machines or drum screening machines. The particle size of the screened dry hydrogel (base polymer) is preferably below 1000 µm, more preferably below 900 µm, most preferably below 850 µm, and preferably above 80 µm, more preferably above 90 µm, most preferably above 100 µm.

Preference is given to hydrogels which, in one embodiment, have a particle size distribution (sieve cuts a), b) and c)) in which a) preferably less than 10% by weight, more preferably less than 5% by weight, most preferably less than 1% by weight, of the polymer particles have a particle size of more than 710 µm, b) preferably at least 80% by weight, more preferably at least 90% by weight, most preferably at least 95% by weight, of the polymer particles have a particle size of from 150 to 710 µm and c) preferably at least 50% by weight, more preferably at least 70% by weight, most preferably at least 90% by weight, of the polymer particles have a particle size of from 300 to 600 µm.

Preference is also given to hydrogels which have a particle size distribution (sieve cuts a), b) and c)) in which a) preferably less than 10% by weight, more preferably less than 5% by weight, most preferably less than 1% by weight, of the polymer particles have a particle size of more than 850 µm, b) preferably at least 80% by weight, more preferably at least 90% by weight, most preferably at least 95% by weight, of the polymer particles have a particle size of from 150 to 850 µm and c) preferably at least 1% by weight, more preferably at least 10% by weight, most preferably at least 20% by weight, of the polymer particles have a particle size of less than 300 µm.

The particle size distribution is determined by the EDANA (European Disposables and Nonwovens Association) recommended test method No. 420.2-02 "Particle size distribution".

According to the invention in step A) the particulate, non-surface-crosslinked, water-absorbing polymer (base polymer) is treated with a mixture comprising an aqueous solvent and at least one salt of a transition metal. The mixture is typically liquid. The salt is present dissolved or suspended in the solvent. In the context of the present invention, a transition metal is understood to mean elements of the periodic table whose atoms have an only partly filled d shell. Preferred transition metals are the elements of the 4th period with atomic numbers 23-29, of the 5th period with atomic numbers 41 to 47 and of the 6th period with atomic numbers 57 to 79.

Preference is given to salts with transition metal cations whose red/ox potential relative to hydrogen is $\geq +0.5$ V. The values reported here for the red/ox potential are based on a 1 normal aqueous solution at 25° C.

Preference is given to inorganic salts with transition metal cations, especially those whose red/ox potential relative to hydrogen is $\geq +0.5$ V. Particular preference is given to inorganic salts with polyvalent transition metal cations, especially those whose red/ox potential relative to hydrogen is $\geq +0.5$ V.

Transition metal cations whose red/ox potential relative to hydrogen is $\geq +0.5$ V, are disclosed, for example, in "Lange's Handbook of Chemistry" (16th edition) 2005 McGraw-Hill, chapter 1.21. Preferred transition metal cations are more preferably $Ag^+$, $Fe^{3+}$, $Cr^{3+}$ and $Ce^{4+}$. The metal cations may be used either alone or in a mixture thereof. In addition, salts of transition metals which have a plurality of different cations, known as mixed salts, are suitable. In this connection, especially those salts which are mixtures of transition metals and ammonium, for example ammonium cerium (IV) nitrate are suitable.

It is also possible to generate the transition metal cations whose red/ox potential relative to hydrogen is $\geq 0.5$ V, directly on the surface of the base polymer particles. In this embodiment, the transition metal cation is used in its reduced form and is oxidized on the surface with the per-compounds specified below or hydrogen peroxide. Preferred transition metal cations in reduced form are $Ag^0$, $Fe^{2+}$, $Cr^{2+}$ and $Ce^{3+}$.

Among the transition metal cations, preference is given to all salts which have a sufficient solubility in the aqueous solvent. Sufficient solubility should be understood to mean that they exhibit, in the aqueous solvent at a temperature of 20° C. and 1 bar, a solubility of $\geq 10$ g/l. Particularly suitable metal salts are those with weakly complexing anions, for example iodide, bromide, chloride, nitrate and sulfate, hydrogensulfate, carbonate, hydrogencarbonate, phosphate, hydrogenphosphate, dihydrogenphosphate and carboxylates, such as formate, acetate, propionate, oxalate and lactate. Especially suitable as salts of transition metals are chlorides, nitrates and sulfates. Very particularly preferred salts of transition metals are ammonium cerium (IV) nitrate, iron(III) sulfate, iron(III) chloride, chromium(III) sulfate and silver nitrate.

Aqueous solvents are understood to mean water and mixtures of water with water-miscible solvents. Water-miscible solvents are understood to mean those which are miscible with water up to an amount of 30% by weight based on the mixture of water and solvent at 25° C. and 1 bar. These include alcohols such as methanol, ethanol, n-propanol, isopropanol, n-butanol, sec-butanol, tert-butanol, 2-methyl-1-propanol, propanediols, butanediols, glycerol and methoxyethanol, glycols such as ethylene glycol, diethylene glycol and polyethylene glycols or polypropylene glycols having a mean molecular weight Mw of ≤1000, ethers and glycol ethers such as dioxane, tetrahydrofuran and polyethylene glycol ether, ketones such as acetone, butanone and cyclohexanone or carboxylic esters, such as ethyl acetate. Particular preference is given to water and water/alcohol mixtures for example water/2-propanol, water/1,2-propanediol and water/1,3-propanediol.

Based on the non-surface-crosslinked, water-absorbing polymer (base polymer) at least 0.0001% by weight, preferably from 0.01 to 5% by weight, more preferably from 0.1 to 1% by weight, of the salt of a transition metal is used.

The base polymer is treated with the salt of a transition metal, for example, by spraying a mixture comprising the aqueous solvent and the salt of a transition metal, preferably a solution of the salt of the transition metal in the aqueous solvent, on to the base polymer. The spraying-on of the mixture is preferably carried out in mixers with moving mixing tools, such as screw mixers, paddle mixers, disk mixers, ploughshare mixers and paddle mixers, mixers with moving vessels, such as drum mixers, tumbler mixers and cone mixers and mixers by gas-induced mixing, such as mixing silos, jet mixers and fluidized bed mixers. Particular preference is given to vertical mixers, very particular preference to ploughshare mixers and paddle mixers. Suitable and known mixers are, for example, Lödige®, Bepex®, Nauta®, Processall® and Schugi® mixers. Very particular preference is given to using high-speed mixers for example of the Schugi-Flexomix® or Turbolizer®type. Very particular preference is given to spraying on a mixture, especially a solution, of the salt of the transition metal in a fluidized bed mixer.

In addition, in step A) the particulate, non-surface-crosslinked, water-absorbing polymer (base polymer) can additionally be treated with at least one compound selected from the group comprising water-soluble per compounds, ethylenically unsaturated carboxylic acids and/or salts thereof, free-radical crosslinkers and deagglomeration agents.

The per-compound may be either an organic or an inorganic per compound. Preference is given to inorganic per compounds such as perborates, persulfates and peroxides. Preference is given to these inorganic per compounds with monovalent cations such as sodium, potassium and/or ammonium. Particular preference is given to persulfates.

Based on the non-surface-crosslinked, water-absorbing polymer (base polymer) preferably from 0.01 to 5% by weight, more preferably from 0.1 to 1% by weight, of the per compound is used.

This treatment of the base polymer with the water-soluble per compound can be effected with the mixture of per compound, the salt of the transition metal and the aqueous solvent or separately, such that there is a kind of mixing only on the base polymer. Preference is given to effecting the addition separately.

Suitable ethylenically unsaturated carboxylic acids are the carboxylic acids listed above under monomers a). Examples include acrylic acid, methacrylic acid, maleic acid, fumaric acid and itaconic acid. Particularly preferred monomers are acrylic acid and methacrylic acid. Very particular preference is given to acrylic acid.

The ethylenically unsaturated carboxylic acids may be used either in their acid form or as salts or mixtures of the two. Preference is given to alkali metal salts and very particularly sodium salts.

Preference is given to using carboxylic acids having a degree of neutralization of from 0 to 80, i.e. the acid or a mixture of salt and acid is used in which up to 80 mol % of the acid is present in the form of salt.

Based on the non-surface-crosslinked, water-absorbing polymer (base polymer) preferably from 0.01 to 5% by weight, more preferably from 0.1 to 1% by weight, of the ethylenically unsaturated carboxylic acid and/or salt thereof is used, this being the total amount of carboxylic acid and salt thereof.

This treatment of the base polymer with the ethylenically unsaturated carboxylic acid and/or salt thereof can be effected with the mixture of carboxylic acid and/or salt thereof, the aqueous solvent and the salt of the transition metal, or with the individual substances, such that there is a kind of mixing only on the base polymer. The ethylenically unsaturated carboxylic acid and/or salt thereof is preferably a constituent of the mixture of aqueous solvent and salt of the transition metal.

Suitable free-radical crosslinkers are the crosslinkers having at least two free-radically polymerizable groups listed above under b). Suitable crosslinkers b) are, for example, ethylene glycol dimethacrylate, diethylene glycol diacrylate, allyl methacrylate, trimethylolpropane triacrylate, triallylamine, tetraallyloxyethane and mixed acrylates which, as well as acrylate groups, comprise further ethylenically unsaturated groups.

Suitable crosslinkers b) are especially N,N'-methylenebisacrylamide and N,N'-methylenebismethacrylamide, esters of unsaturated mono- or polycarboxylic acids of polyols such as diacrylate or triacrylate and allyl compounds. Very particularly preferred crosslinkers b) are the polyethoxylated and/or propoxylated glycerols which have been esterified with acrylic acid or methacrylic acid to give di- or triacrylates, and the polyethylene glycols which have been esterified with acrylic acid or methacrylic acid to give diacrylates.

Based on the non-surface-crosslinked, water-absorbing polymer (base polymer) preferably from 0.001 to 0.5% by weight, more preferably 0.01 to 0.1% by weight of the crosslinker is used.

This treatment of the base polymer with the free-radical crosslinker can be effected with the mixture of crosslinker, the aqueous solvent and the transition metal salt, or with the individual substances, such that there is a kind of mixing only on the base polymer. The crosslinker is preferably a constituent of the mixture of aqueous solvent and the salt of the transition metal.

More preferably, in step A) the base polymer is additionally treated with at least one ethylenically unsaturated carboxylic acid and/or salt thereof and/or a free-radical crosslinker.

Most preferably, the base polymer, in step A) is additionally treated with at least one free-radical crosslinker.

More preferably, in step A), the base polymer is additionally treated with at least one deagglomeration agent.

Deagglomeration agents in the context of the present invention are fine substances in powdery or fibrous form which are inert with respect to the preparation conditions of the components and of the mixtures and may be of organic or inorganic nature. Examples of such additives are: fine silicon dioxide, fumed silicas, precipitated silicas in hydrophilic or hydrophobic polymorphs, zeolites, titanium dioxide, zirconium dioxide, zinc oxide, talc, bentonites of any type, cellulose, silicates of any type, guar flour, tara flour, carob flour, all kinds of starches, clays, barium sulfate, calcium sulfate.

Likewise deagglomeration agents in the context of the present invention are liquid substances which are inert with respect to the preparation conditions of the components and of the mixtures and may be of organic or inorganic nature. Examples of such additives are: silicones, for example in the form of oils and oil emulsions in water, waxes, for example natural and synthetic paraffins with and without functional groups, metal soaps, for example metal salts of fatty acids, such as calcium stearate, lead stearate, magnesium stearate, aluminum stearate and zinc stearate, polymers, for example polyvinyl alcohol, polyesters and polyolefins and nonionic surfactants, preferably polyoxyethylene alkyl ethers as described in WO 2006/062258 as assistants.

Based on the non-surface-crosslinked, water-absorbing polymer (base polymer) preferably from 0.001 to 10% by weight, more preferably 0.01 to 5% by weight of the deagglomeration agent is used.

This treatment of the base polymer with the deagglomeration agent can be effected with the mixture of deagglomeration agent, the aqueous solvent and the transition metal salt, or with the individual substances, such that there is a kind of mixing only on the base polymer. Preference is given to adding the deagglomeration agent separately.

When the content of aqueous solvent in the treated base polymer falls below a value of 3% by weight after the treatment step A), it is advisable to moisten the treated base polymer. This can occur especially in the preferred variant, in which a fluidized bed mixer is selected, or in a variant in a heated mixer. The moistening can be accomplished with one of the abovementioned aqueous solvents, preferably water. The moistening, preferably spraying, is effected up to a solvent content of from >3 to 20% by weight, preferably from 5 to 15% by weight, based on the moistened base polymer.

The irradiation is effected by customary processes known to those skilled in the art. UV radiation is understood by the person skilled in the art to mean radiation of wavelengths from 1 to 400 nm, preferably from 150 to 350 nm. Suitable for irradiation are, for example, conventional UV radiators such as high-pressure, medium-pressure and low-pressure mercury radiators, and also fluorescent tubes, pulse radiators, lasers, metal halide radiators, xenon radiators and halogen radiators or excimer radiators. The radiation dose typically sufficient for crosslinking is within the range from 10 to 5000 mJ/cm$^2$. The irradiation time is from 0.1 seconds to 60 minutes, preferably from 0.5 seconds to 30 minutes, especially from 1 second to 15 minutes.

The polymer particles can be irradiated either in suspension with a liquid or in a gas or gas mixture. When the irradiation is effected in suspension with a liquid, the suspension should be transparent to UV radiation, i.e. not extinguish more than 10% of the 400 nm wavelength. Suitable liquids mentioned by way of example are heptane or cyclohexane. Preference is given to irradiating the polymer particles in a gaseous environment which preferably comprises water vapor. Preferred gases or gas mixtures are air, water vapor and/or inert gas, such as nitrogen, carbon dioxide, noble gases or combustion gases, and also mixtures thereof. The gas mixture more preferably comprises water vapor. Very particular preference is given to performing the irradiation of the polymer particles in an atmosphere composed of water vapor-containing air with a relative air humidity of from 20 to 100%.

In the embodiment in which the polymer particles are irradiated in a gas/gas mixture, the pressure in the gas space is adjusted to a value in the range from 0.001 to 10 bar, preferably from 0.1 to 3 bar, more preferably from 0.5 to 1.5 bar and most preferably to standard pressure.

The temperature selected for the irradiation mixture is a value in the range from 0° C. to 250° C., preferably from 20° C. to 200° C., more preferably from 40° C. to 180° C. and most preferably from 60° C. to 140° C. According to the energy input, there may be heating of the irradiation mixture. If appropriate, it may be advisable to cool or to heat it to the desired value.

In a further embodiment of the invention, in addition to the UV irradiation, treatment by IR radiation can also be effected. The IR irradiation can be effected before, in parallel to and/or after the UV irradiation. IR radiation is understood by the person skilled in the art to mean radiation of wavelengths from 780 nm to 1 mm.

After the irradiation in process step B), the treated polymer, in a preferred variant (process step C), is dried. Preference is given to drying down to a water content of ≤20% by weight, preferably of ≤5% by weight, especially of ≤3% by weight. This drying is effected, for example, by thermal treatment at a temperature of at least 40° C. and at most 250° C., preferably within a temperature range from 60 to 200° C., more preferably from 80° C. to 180° C.

The mean residence time (i.e. the average residence time of the individual water-absorbing polymer particles) of the polymer obtained from step C) in the drier is generally at least 1 minute, preferably at least 3 minutes and more preferably at least 5 minutes, and generally at most 6 hours, preferably at most 2 hours and more preferably at most 1 hour.

The thermal treatment is effected, for example, in a heated mixer ("drier") such as staged driers, rotary tube driers or heatable screws, preferably in contact driers. Preference is given to the use of driers in which the product is agitated, i.e. heated mixers, more preferably paddle driers, most preferably disk driers. Suitable driers are, for example, Bepex® driers and Nara® driers. Moreover, it is also possible to use convection driers such as belt driers and fluidized bed driers. However, the drying can also be effected convectively in the mixer itself, for example by combining the heating of the jacket with the supply of a preheated gas, such as air.

Thereafter, it may be advantageous to cool the inventive water-absorbing material. The cooling can be effected continuously or discontinuously; conveniently, the product, for this purpose, is conveyed continuously into a cooler connected downstream of the drier. To this end, any apparatus known for the removal of heat from powders can be used, especially any apparatus mentioned above as a drying apparatus, provided that it is not supplied with a heating medium but rather with a cooling medium, for instance with cooling water, such that no heat is introduced into the water-absorbing polymers via the walls and, according to the construction, also via the mixing units or other heat exchange surfaces, but rather is removed therefrom. Preference is given to the use of coolers in which the product is agitated, i.e. cooled mixers, for example paddle coolers, disk coolers or paddle coolers, for instance in Nara® or Bepex® coolers. The water-absorbing material can also be cooled in a fluidized bed by blowing in a cooled gas such as cold air. The conditions of the cooling are adjusted such that a water-absorbing material with the temperature desired for the further processing is obtained. Typically, a mean residence time in the cooler of generally at least 1 minute, preferably at least 3 minutes and more preferably at least 5 minutes, and generally at most 6 hours, preferably 2 hours and more preferably at most 1 hour is established, and the cooling performance is such that the resulting product has a temperature of generally at least 0° C., preferably at least 10° C. and more preferably at least 20° C., and generally at most 100° C., preferably at most 80° C. and more preferably at most 60° C.

Optionally, a further modification of the water-absorbing material can also be effected by adding a deagglomeration agent. Suitable deagglomeration agents are those mentioned above.

If appropriate, the water-absorbing material is provided with further customary additives and assistants which influence storage or handling properties. Examples thereof are colorings, opaque additives in order to improve the visibility of swollen gel, which is desirable in some applications, additives for improving the flow behavior of the powder or the like. Often, dedusting agents or dust binding agents are added to the water-absorbing material. dedusting agents or dust binding agents are known; for example polyether glycols such as polyethylene glycol having a molecular weight of from 400 to 20 000 g/mol, polyols such as glycerol, sorbitol, neopentyl glycol or trimethylolpropane, which are optionally also 7- to 20-tuply ethoxylated, are used. A finite water content of the water-absorbing material can also be established by adding water, if desired.

The solids, additives and assistants can each be added in separate process steps; however, the most convenient method is usually to add them to the water-absorbing material in the cooler, for instance by spraying on a solution or adding them in fine solid form or in liquid form.

The water-absorbing material is, if appropriate, typically ground and/or screened. Grinding is typically not required here, but the screening-off of agglomerates formed or fines is usually appropriate to establish the desired particle size distribution of the product. Agglomerates and fines are either discarded or preferably are recycled into the process in a known manner and at a suitable point; agglomerates after comminution. The particle size of the water-absorbing material is preferably at most 1000 μm, more preferably at most 900 μm, most preferably at most 850 μm, and preferably at least 80 μm, more preferably at least 90 μm, most preferably at least 100 μm. Typical sieve cuts are for example from 106 to 850 μm or from 150 to 710 μm.

The inventive water-absorbing material exhibits a good absorption under pressure (AUP) and can be produced within a short processing time and without thermal stress. In the process according to the invention, by virtue of the irradiation, a crosslinking reaction likewise takes place at the surface of the base polymer. It is assumed that it is not a crosslinking by virtue of the condensation reactions via the acid radicals, but rather a free-radical reaction probably takes place.

Additionally found have been hygiene articles which comprise the inventive water-absorbing material. Inventive hygiene articles are, for example, those intended for use in the case of light or heavy incontinence, for instance pads for heavy or light incontinence, incontinence pants, and additionally diapers for babies and infants, or else feminine hygiene articles such as pads, sanitary napkins or tampons. Such hygiene articles are known.

"Diapers for babies and infants", "feminine hygiene articles" and "incontinence articles" refers to devices that absorb and retain bodily liquids (such as blood and urine), and more specifically, refers to devices that are placed against or in proximity to the body of the wearer to absorb and contain the various exudates discharged from the body. "Diaper for babies and infants" refers to an absorbent article generally worn about the lower torso. The term "diaper for babies and infants" comprise taped diapers, which are applied to the wearer using tapes or other suitable closing means. The term "diaper for babies and infants" also comprises pull-on pants, and pull-on training pants, which are pant-like diapers having fixed sides and leg openings. Such pant-like diapers are placed in position on the wearer by inserting the wearer's legs into the leg openings and sliding the pant-like diaper into position about the wearer's lower torso.

"Feminine hygiene articles" refers to sanitary napkins, panty liners, interlabial devices and tampons.

"Incontinence articles" refers to refers to an absorbent article generally worn about the lower torso of adults. The term "incontinence articles" comprise taped diapers, which are applied to the adult wearer using tapes or other suitable closing means. The term "incontinence articles" also comprises pull-on pants for adults, and pull-on training pants for adults, which are pant-like diapers for adults having fixed sides and leg openings. Such pant-like diapers are placed in position on the adult wearer by inserting the wearer's legs into the leg openings and sliding the pant-like diaper into position about the wearer's lower torso. The term "incontinence articles" also comprises adult incontinent briefs.

The diapers for babies and infants, feminine hygiene articles and incontinence articles of the present invention are preferably disposable. "Disposable" is used herein to describe articles that are generally not intended to be laundered or otherwise restored or reused (i.e., they are intended to be discarded after a single use and, preferably, to be recycled, composted or otherwise disposed of in an environmentally compatible manner).

The inventive hygiene articles differ from known hygiene articles in that they comprise the inventive water-absorbing material. Also found has been a process for producing the hygiene articles, which comprises using, in the production of the hygiene article in question, at least one inventive water-absorbing material. Otherwise, processes for producing hygiene articles using water-absorbing material are known.

The present invention further relates to the use of the inventive water-absorbing material for absorption of water-comprising fluids. The inventive water-absorbing material may additionally be used in other fields of industry in which liquids, especially water or aqueous solutions, are absorbed. These fields are, for example, storage, packaging, transport (as constituents of packaging material for water- or moisture-sensitive articles, for instance for flower transportation and also as protection against mechanical impacts); animal hygiene (in cat litter); food packaging (transportation of fish, fresh meat; absorption of water, blood in fresh fish or meat packaging); medicine (wound plasters, water-absorbing material for burn dressings or for other weeping wounds), cosmetics (carrier material for pharmaceuticals and medicaments, rheumatic plasters, ultrasound gel, cooling gel, cosmetic thickeners, sunscreen); thickeners for oil/water or water/oil emulsions; textiles (moisture regulation in textiles, shoe inserts, for evaporative cooling, for instance in protective clothing, gloves, headbands); chemical engineering applications (as a catalyst for organic reactions, for immobilization of large functional molecules such as enzymes, as an adhesive agent in agglomerations, heat stores, filtration aids, hydrophilic component in polymer laminates, dispersant, liquefier); as assistants in powder injection molding, in the building and construction industry (installation, in loam-based renders, as a vibration-inhibiting medium, assistant in tunnel excavations in water-rich ground, cable sheathing);

water treatment, waste treatment, water removal (deicing agent, reusable sandbags); cleaning; agrochemical industry (irrigation, retention of melt water and dew deposits, composting additive, protection of forests from fungal/insect infestation, delayed release of active ingredients to plants); for firefighting or for fire protection; coextrusion agent in thermoplastic polymers (for example for hydrophilizing multilayer films); production of films and thermoplastic shaped bodies which can absorb water (for instance films which store rain and dew water for agriculture; films comprising water-absorbing polymers for keeping fruit and vegetables which are packaged in moist films fresh; water-absorbing polymer-polystyrene coextrudates, for example for food packaging such as that of meat, fish, poultry, fruit and vegetables); or as a carrier substance in active ingredient formulations (pharmaceuticals, crop protection).

Test Methods

Absorption under pressure ("AUP", "Absorption Under Pressure"):

The AAP (0.3 psi) is determined by the EDANA (European Disposables and Non-wovens Association, Avenue Eugène Plasky 157, 1030 Brussels, Belgium) recommended test method No. 442.2-02, obtainable therefrom.

EXAMPLES

A) Preparation of the Base Polymer

A Lödige VT 5R-MK ploughshare kneader (capacity 5 liters) was initially charged with a reaction mixture composed of 183 g of water, 239 g of acrylic acid and 2148 g of a 37.3% by weight sodium acrylate solution (100 mol % neutralized) and also 2.8 g of 3-tuply ethoxylated glyceryl triacrylate, and inertized by sparging with nitrogen for 20 minutes. The reaction mixture was cooled externally such that the subsequent addition of initiator was effected at approx. 20° C. With stirring, the initiators (2.39 g of sodium persulfate (dissolved in 13.53 g of water), 0.05 g of ascorbic acid (dissolved in 10.18 g of water)) and 0.14 g of 30% by weight hydrogen peroxide (dissolved in 1.28 g of water) were added to the kneader in rapid succession. The reaction set in rapidly and, on attainment of an internal temperature of 30° C., the jacket of the kneader was heated with heat carrier medium at 80° C. in order to conduct the reaction to the end as adiabatically as possible. On attainment of the maximum temperature, the gel formed was cooled down in the kneader to below 50° C. by means of cooling liquid (−12° C.) and then discharged.

The gel was distributed on two metal sheets with a wire base and dried in a forced-air drying cabinet at 160° C. Subsequently, a Retsch laboratory ultracentrifugal mill was used to comminute it to a particle size of from 150 to 600 µm.

The base polymer GP-A thus prepared had an AAP (0.3 psi) of 10.9 g/g.

Example 1

A 20 ml beaker was charged with 3 g of acetone, 7 g of demineralized water and 2.5 g of ammonium cerium(IV) nitrate which were stirred for 10 min. 2 g of the resulting solution were sucked in with a syringe (capacity 10 ml with steel cannula).

20 g of the base polymer GP-A prepared according to Example A) were introduced into a Waring laboratory blender. The blender was set to level I and the 2 g of solution was sprayed on to the mixing base polymer all at once via the syringe. The sprayed base polymer BP-1 was thus obtained. The sprayed base polymer BP-1, immediately after the spraying, was spread out very uniformly over the area of a Petri dish (diameter 12 cm). A Höhnle UV radiator (UVA-Spot 400, power 400 watts) was then placed immediately over the filled Petri dish at a distance of 5 cm and the polymer sample was irradiated for 1 min. To this route the surface-crosslinked polymer OP-2 was obtained.

The resulting product (designated as OP-1) exhibited good performance properties. In addition, the product OP-1 was dried in a forced-air drying cabinet at 105° C. for 1 hour and, in this way the dry material TG-1 was obtained.

The measurement of the AAP (0.3 psi) gave a value of 16.1 g/g for the sprayed base polymer BP-1, a value of 21.4 g/g for the irradiated polymer OP-1, and a value of 23.2 g/g for the dry material TG-1.

Example 2 (Non-Inventive)

A 20 ml beaker was charged with 3 g of acetone, 7 g of demineralized water and 0.5 g of oxazolidinone which were stirred for 10 min. 2 g of the resulting solution were sucked in with a syringe (capacity 10 ml with steel cannula).

20 g of the base polymer GP-A were introduced into a Waring laboratory blender. The blender was set to level I and the 2 g of solution were sprayed on to the mixing base polymer all at once via the syringe. The sprayed base polymer BP-2 was thus obtained. The sprayed base polymer BP-2, immediately after the spraying, was spread out very uniformly over the area of a Petri dish (diameter 12 cm). The polymer sample was then placed into a forced-air drying cabinet preheated to 200° C. and removed again after 1 min. In this way, the surface-crosslinked polymer OP-2 was obtained.

The measurement of the AAP (0.3 psi) gave a value of 9.4 g/g for the sprayed base polymer BP-2, and a value of 10.7 g/g for the surface-crosslinked polymer OP-2.

Example 3 (Non-Inventive)

A 20 ml beaker was charged with 3 g of acetone, 7 g of demineralized water and 2.5 g of a 30% by weight aqueous hydrogen peroxide solution which were stirred for 10 min.

2 g of the resulting solution were sucked in with a syringe (capacity 10 ml with steel cannula).

20 g of the base polymer GP-A were introduced into a Waring laboratory blender. The blender was set to level I and the 2 g of solution were sprayed on to the mixing base polymer all at once via the syringe. The sprayed base polymer BP-3 was thus obtained. The sprayed base polymer BP-3, immediately after the spraying, was spread out very uniformly over the area of a Petri dish (diameter 12 cm). A Höhnle UV radiator (UVA-Spot 400, power 400 watts) was then placed immediately above the filled Petri dish at a distance of 5 cm and the polymer sample was irradiated for 1 min. In this way, the irradiated polymer OP-3 was obtained.

The measurement of the AAP (0.3 psi) gave a value of 10.4 g/g for the sprayed base polymer BP-3, and a value of 8.0 g/g for the irradiated polymer OP-3.

Example 4

A 20 ml beaker was charged with 3 g of acetone, 7 g of demineralized water and 2.5 g of iron(III) chloride and 2.5 g of acrylic acid, which were stirred for 10 min. 2 g of the resulting solution were sucked in with a syringe (capacity 10 ml with steel cannula).

20 g of the base polymer GP-A prepared according to Example A) were introduced into a Waring laboratory blender. The blender was set to level I and the 2 g of solution were sprayed on to the mixing base polymer all at once by means of the syringe. The sprayed base polymer BP-4 was thus obtained.

The sprayed base polymer BP-4, immediately after the spraying, was spread out very uniformly over the area of a Petri dish (diameter 12 cm). A Höhnle UV radiator (UVA-Spot 400, power 400 watts) was then placed immediately over the filled Petri dish at a distance of 5 cm and the polymer sample was irradiated for 1 min. The resulting product is designated as OP-4. In addition, the product OP-4 was dried in a forced-air drying cabinet at 105° C. for 1 hour and, in this way, the dry material TG-4 was obtained.

The measurement of the AAP (0.3 psi) gave a value of 14.7 g/g for the sprayed base polymer BP-4, a value of 22.9 g/g for the irradiated polymer OP-4, and a value of 26.3 g/g for the dry material TG-4.

The invention claimed is:

1. A water-absorbing material prepared by a process comprising
   A) treating a particulate, non-surface-crosslinked, water-absorbing polymer with a mixture comprising an aqueous solvent and at least one salt of a transition metal, and
   B) irradiating the polymer treated according to A) with UV radiation.

2. The water-absorbing material according to claim 1, wherein the salt of the transition metal has a cation whose red/ox potential relative to hydrogen is ≥+0.5 V.

3. The water-absorbing material according to claim 1, wherein the salt of the transition metal is an inorganic salt.

4. The water-absorbing material according to claim 1, wherein the salt of the transition metal has a solubility in aqueous solvents of ≥10 g/l.

5. The water-absorbing material according to claim 1, wherein from 0.1 to 5% by weight of the salt of the transition metal, based on the non-surface-crosslinked water-absorbing polymer, is applied.

6. The water-absorbing material according to claim 1, wherein the mixture comprising the aqueous solvent and the salt of a transition metal is sprayed onto the particulate, non-surface-crosslinked, water-absorbing polymer in a fluidized bed.

7. The water-absorbing material according to claim 1, wherein in step A), the non-surface-crosslinked water-absorbing polymer is treated with at least one ethylenically unsaturated carboxylic acid and/or alkali metal salt thereof and/or a free-radical crosslinker.

8. The water-absorbing material according to claim 1, wherein in step A), the non-surface-crosslinked water-absorbing polymer is treated with at least one free-radical crosslinker.

9. The water-absorbing material as claimed in claim 1, wherein at least one deagglomeration agent is added in step A).

10. A water-absorbing material prepared by a process comprising
    A) treating a particulate, non-surface-crosslinked, water-absorbing polymer with a mixture comprising an aqueous solvent and at least one salt of a transition metal
    B) irradiating the polymer treated according to A) with UV radiation, and
    C) subsequently drying the material obtained according to B).

11. A process for producing a water-absorbing material, comprising
    A) treating a particulate, non-surface-crosslinked, water-absorbing polymer with a mixture comprising an aqueous solvent and at least one salt of a polyvalent transition metal,
    B) irradiating the polymer treated according to A) with UV radiation and, optionally
    C) subsequently drying the material obtained according to B).

* * * * *